(12) United States Patent
Whalen et al.

(10) Patent No.: US 6,719,709 B2
(45) Date of Patent: Apr. 13, 2004

(54) DIAGNOSTIC URETHRAL ASSEMBLY AND METHOD

(75) Inventors: Mark J. Whalen, Alexandria, MN (US); Lloyd K. Willard, Miltona, MN (US); John M. Reid, Garfield, MN (US)

(73) Assignee: AbbeyMoor Medical, Inc., Miltona, MN (US)

( * ) Notice: Subject to any disclaimer, the term of this patent is extended or adjusted under 35 U.S.C. 154(b) by 114 days.

(21) Appl. No.: 09/943,975

(22) Filed: Aug. 31, 2001

(65) Prior Publication Data

US 2002/0065476 A1 May 30, 2002

Related U.S. Application Data

(60) Provisional application No. 60/229,143, filed on Aug. 31, 2000, and provisional application No. 60/264,700, filed on Jan. 30, 2001.

(51) Int. Cl.[7] .................. A61B 5/103; A61M 27/00
(52) U.S. Cl. ........................... 600/587; 604/544
(58) Field of Search .............. 600/561, 29, 587, 600/591, 593; 604/264, 544, 96.01, 162.02

(56) References Cited

U.S. PATENT DOCUMENTS

| | | |
|---|---|---|
| 2,687,131 A | 8/1954 | Raiche |
| 3,208,102 A | 9/1965 | Rubio |
| 3,227,154 A | 1/1966 | Cook |
| 3,513,269 A | 5/1970 | Wilson |
| 3,591,290 A | 7/1971 | Zinner et al. |
| 3,742,960 A | 7/1973 | Dye et al. |
| 3,789,518 A | 2/1974 | Chase |
| 3,848,346 A | 11/1974 | Mackey |
| 3,908,637 A | 9/1975 | Doroshow |
| 4,121,572 A | 10/1978 | Krzeminski |
| 4,217,911 A | 8/1980 | Layton |
| 4,301,811 A | 11/1981 | Layton |
| 4,312,826 A | 1/1982 | Colvin |
| 4,407,301 A | 10/1983 | Streisinger |
| 4,484,585 A | 11/1984 | Baier |
| 4,500,313 A | 2/1985 | Young |
| 4,538,621 A | 9/1985 | Jarczyn |
| 4,553,959 A | 11/1985 | Hickey et al. |
| 4,612,939 A | 9/1986 | Robertson |
| 4,726,748 A | 2/1988 | Lazik et al. |
| 4,781,677 A | 11/1988 | Wilcox |
| 4,790,328 A | 12/1988 | Young |
| 4,824,071 A | 4/1989 | Duffy et al. |
| 4,825,875 A | 5/1989 | Ninan et al. |
| 4,873,990 A | 10/1989 | Holmes et al. |
| 4,932,958 A | 6/1990 | Reddy et al. |
| 4,946,449 A | 8/1990 | Davis, Jr. |
| 4,973,301 A | * 11/1990 | Nissenkorn ............ 604/8 |
| 5,071,429 A | 12/1991 | Pinchuk et al. |

(List continued on next page.)

*Primary Examiner*—Charles Marmor
(74) *Attorney, Agent, or Firm*—Nawrocki, Rooney & Sivertson, P.A.

(57) ABSTRACT

A diagnostic urethral assembly includes an elongate body having a fluid passageway and an elongate support member selectively positionable within the fluid passageway of the elongate body. The elongate body has a radially responsive wall segment that is being positionable within a lower urinary tract such that the radially responsive wall segment is adjacent a prostatic urethra. The elongate body is adapted to be in fluid communication with a bladder. The assembly has a first condition wherein the elongate support member is translatable relative to the elongate body so as to permit sequential and incremental radial compression of the radially responsive wall segment by the prostatic urethra in furtherance of defining architecture associated with the prostatic urethra and a second condition wherein fluid distally introduced into the elongate body radially expands the radially responsive wall segment into conforming engagement with the prostatic urethra in furtherance of obtaining a mold of same.

31 Claims, 7 Drawing Sheets

U.S. PATENT DOCUMENTS

| | | |
|---|---|---|
| 5,112,306 A | 5/1992 | Burton et al. |
| 5,250,029 A | 10/1993 | Lin et al. |
| 5,254,089 A | 10/1993 | Wang |
| 5,295,979 A | 3/1994 | DeLaurentis et al. |
| 5,320,605 A | 6/1994 | Sahota |
| 5,322,501 A | 6/1994 | Mahmud-Durrani |
| 5,360,402 A | 11/1994 | Conway et al. |
| 5,385,563 A | 1/1995 | Gross |
| 5,403,280 A | 4/1995 | Wang |
| 5,427,115 A | 6/1995 | Rowland et al. |
| 5,518,407 A | 5/1996 | Greenfield et al. |
| 5,609,583 A | 3/1997 | Hakki et al. |
| 5,657,764 A | 8/1997 | Coulter et al. |
| 5,718,686 A * | 2/1998 | Davis .................... 604/101.05 |
| 5,735,831 A | 4/1998 | Johnson et al. |
| 5,752,522 A | 5/1998 | Murphy |
| 5,766,209 A * | 6/1998 | Devonec ........................ 604/8 |
| 5,776,081 A | 7/1998 | Kreder |
| 5,785,641 A * | 7/1998 | Davis .......................... 600/30 |
| 5,864,961 A | 2/1999 | Vaughan |
| 5,997,796 A | 12/1999 | Moore |
| 6,004,290 A | 12/1999 | Davis |
| 6,056,699 A | 5/2000 | Sohn et al. |
| 6,083,179 A | 7/2000 | Oredsoon |
| 6,096,013 A | 8/2000 | Hakky et al. |
| 6,447,462 B1 | 9/2002 | Wallace et al. |
| 6,494,879 B2 * | 12/2002 | Lennox et al. .................. 606/8 |

* cited by examiner

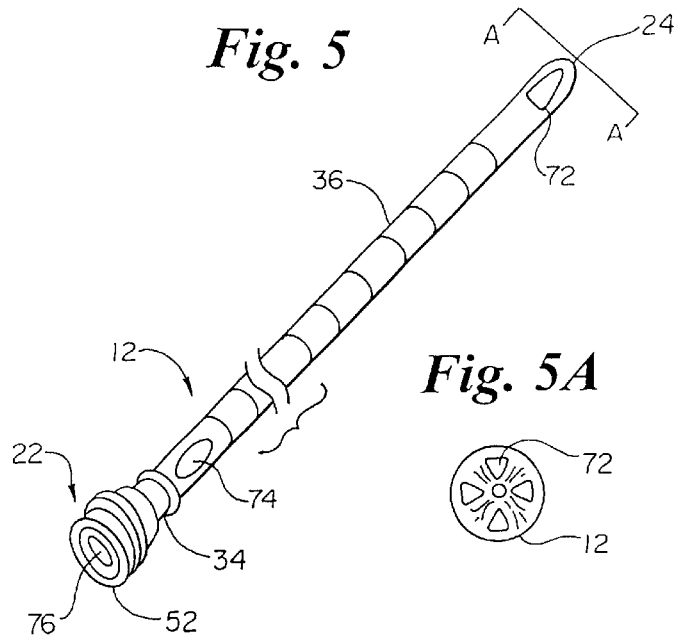
*Fig. 5*
*Fig. 5A*
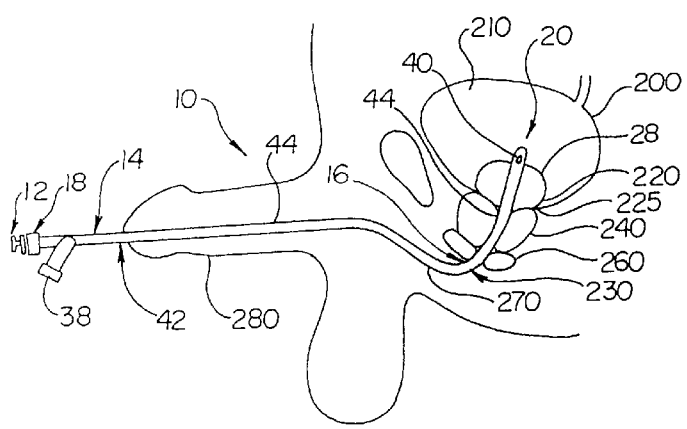
*Fig. 6*

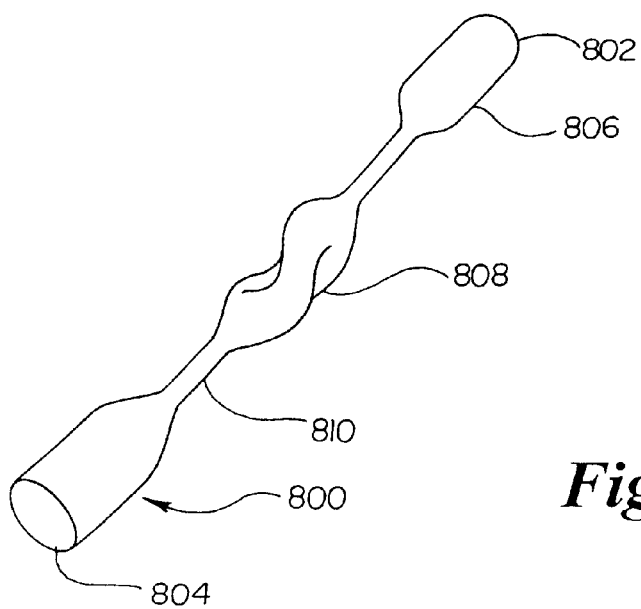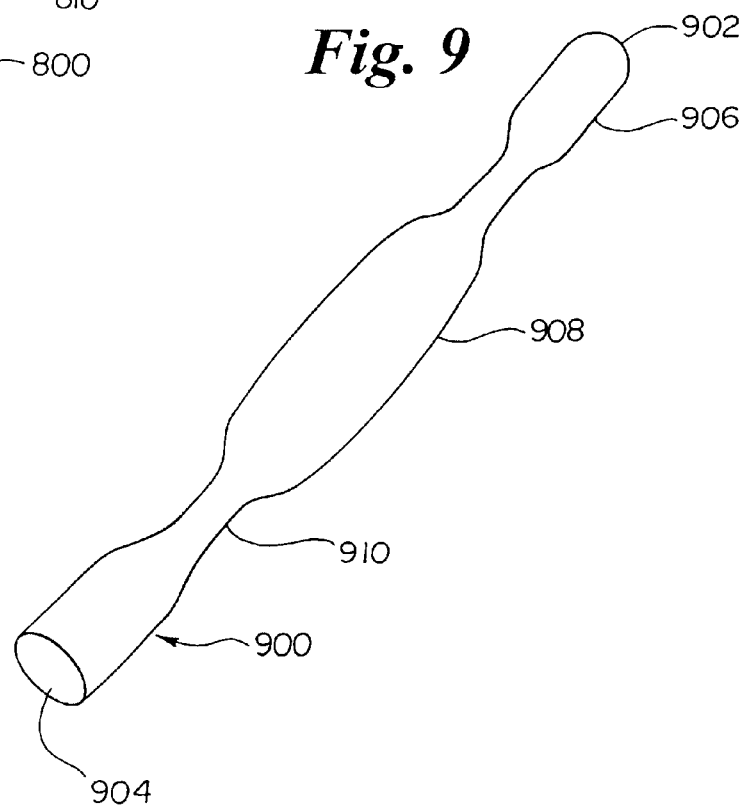

DIAGNOSTIC URETHRAL ASSEMBLY AND METHOD

This is a regular application filed under 35 U.S.C. §111(a) claiming priority under 35 U.S.C. §119(e)(1), of provisional application Ser. No. 60/229,143 having a filing date of Aug. 31, 2000, filed under 35 U.S.C. §111(b), as well as provisional application Ser. No. 60/264,700 having a filing date of Jan. 30, 2001, filed under 35 U.S.C. §111(b).

TECHNICAL FIELD

The present invention generally relates to medical devices, more particularly to a diagnostic urethral assembly and attendant methodology for assessing lower urinary tract symptoms.

BACKGROUND OF THE INVENTION

A diagram of the male urinary bladder and urinary passage (i.e., the lower urinary tract) is presented in FIG. 1. The bladder 200 temporarily stores urine 210 and periodically expels it when the bladder neck 220 opens, as the bladder 200 contracts. Urine 210 passes through the prostatic urethra 230, which is completely surrounded by the prostate 240. The distal limit of prostate 240 is marked by a small projection called the verumontanum 250. This is a important landmark because distal thereto, is the external urethral sphincter 260, which relaxes prior to the urination process beginning. Beyond this is the urethra 270, affording a free passage of urine 220 external to body, beyond the external urethral meatus 280.

Presently, millions of men in the United States alone exhibit some form of lower urinary tract symptoms (LUTS), with bladder outlet obstructions (BOOs) being a major subgroup of LUTS. BOOs are primarily caused by the enlargement of the prostate gland (e.g., benign prostate hyperplasia (BHP)) which results in radial compression of the urethra surrounded thereby (i.e., the prostatic urethra), thus obstructing (i.e., constricting) urine flow, resulting in incomplete emptying of the bladder (i.e., there being what is clinically referred to as a "post void residual" (PVR) remaining in the bladder). Persons exhibiting an abnormal PVR will often need to urinate more frequently, and are likely to experience other physical discomfort, such as frequent urges to urinate, and physical exhaustion due to sleep deprivation, a condition clinically referred to as nocturia. Heretofore, such symptoms would be treated using surgical procedures such as transurethral resection of the prostate (TURP), or non-surgical procedures such as thermal treatment of the prostate.

As bladder outlet obstruction patients are a subgroup of patients with LUTS, proper treatment of the specific problem requires a knowledge of complete urodynamic status of the patient in order determine the cause of the symptoms. Causes may include bladder deficiencies such as bladder decompensation or hypertrophy, sphincter dysnergia, prostatic obstruction, urethral lesions and others.

There are diagnostic procedures available to clinical urologists, the purpose of which is to assess the physiologic properties of the lower urinary tract and symptoms related thereto. Such tests, which address the filling/emptying conditions (i.e., dynamics) of the bladder, include, but are not limited to, the use of video fluoroscopy simultaneously with the holding and release of urine, cystometry, urethral pressure profiling, ultrasonic volume assessments, and uroflowmetry. The subject invention provides additional heretofore unknown diagnostic options which allow for relatively simple and increased understanding of the urinary tract by assessing the elements (i.e., structures or architecture) thereof, more particularly the prostatic urethra and their influence on urine flows.

One of the urodynamic tests frequently performed in urodynamic investigations is cystometry, a test of bladder function in which pressure and volume of fluid in the bladder is measured during filling, storage, and voiding. A cystometry study is performed to diagnose problems with urination, including incontinence, urinary retention, and recurrent urinary tract infections. Urinary difficulties may occur because of weak or hyperactive sphincter or detrusor (i.e., the main muscle of the bladder wall), or incoordination of their two activities. Infection of the bladder or urethra may cause incontinence, as can obstruction of the urethra from scar tissue, prostate enlargement, or other benign or cancerous growths. Loss of sensation due to nerve damage can lead to chronic overfilling.

This test of detrusor muscle function generally consists of distending the bladder with a known volume of a fluid (i.e., liquid (e.g., water, saline, etc.) or gas (e.g., air, carbon dioxide, etc.)) while recording the intravesical pressure. The desired fluid may be introduced either through the urethra or suprapubically, in most cases the fluid is instilled through a double lumen catheter at a rate of approximately 10 cc/min, with the catheter employed permitting both filling of the bladder and recording of bladder pressure. As the bladder is composed mostly of small muscles, which are to a large degree under voluntary control, and muscle bundles which run in different directions and from layer to layer, adaptation of the bladder to changing fluid volume is primarily due to the viscal-elastic property of the organ. The bladder wall, in a healthy individual, is able to expand without any significant increase in tension as the bladder fills with fluid.

When the bladder is artificially filled, the pressure which is required to fill that bladder will provide for clinical characterization of the bladder and its general health. If a bladder is non-compliant, the pressure to fill the bladder will increase prematurely. If it is decompensated, meaning it has lost some of its tone, the filling pressure will be minimal while the bladder volume may be large. When the bladder is becoming full, the patient will experience a strong sensation of needing to urinate.

In a typical cystometric study, the filling phase looks at the bladder's ability to comply to increased volume. The detrusor muscle normally expands as volume increases so that the bladder initially rises very little in pressure to the time the patient voids (i.e., in a plot of pressure against volume of contents during filling (i.e., a "cystometrogram" (CMG)), the early portion of this graph is substantially flat for a healthy individual). The normal bladder should not begin contractions during filling and should initially expand without resistance. A feeling of fullness occurs with a volume of about 100–200 ml, with an adult bladder capacity on the order of about 300–500 ml. The sphincter should relax and open when the patient wills it, accompanied by detrusor contractions. During voiding, detrusor contraction should be smooth and lead to a steady urine stream.

If bladder pressure continually rises during filling, it can be due to a number of factors which would bear further investigation. For instance, inability of the bladder to relax during filling, or low bladder volume, may indicate interstitial cystitis, prostate enlargement, or bladder cancer. Contraction of the bladder during filling (i.e., any rise in bladder pressure that is not accompanied by a rise in abdominal pressure) may be due to irritation from infection or cysts, obstruction of the bladder outlet, or neurological disease such as stroke, multiple sclerosis, or spinal cord injury. Diminished sensation may occur with nerve lesions, peripheral neuropathy, or chronic overfilling.

A procedure generically referred to as "bedside cystometry" is used to determine, at a basic level, whether the bladder appears decompensated. This is accomplished by simply filling the bladder through a catheter with a known fluid volume, often ranging from about 250–400 ml. The patient is ask to inform the physician when he or she has a strong urge to urinate. Should the patient lack such urge, even when the bladder accommodates the introduced fluid volume, it is likely that some degree of bladder decompensation is present. As the bladder capacities increase, the probability of decompensation increases.

Whether monitoring filling pressures and volumes for the purpose of bladder characterization, or at a bedside procedure which only monitors initiation of flows, information with regard to bladder emptying is typically not acquired. Even if such information were acquired, meaningful diagnosis of BOOs is not possible.

Another standard urodynamic test is called the urethral pressure profile (UPP), (i.e., perfusion urethral profilometry), a procedure which assesses urethral integrity by determining the inward pressure of the urethra continuously along its length (i.e., a measure of the urethra's response to distention). This test is especially pertinent with respect to patients with incontinence or obstructive symptomatology. Usually a profile of urethral pressure may be obtained by the withdrawal of a pressure recording catheter from the bladder through the urethra. Several methods of profilometry exist including measurement of pressure inside of a balloon which traverses the urethra and also the measurement of the urethral pressure that is transmitted against a fluid or gas that is infused through a small catheter traversing the urethra.

The UPP is typically carried out by inserting a catheter having a side opening and a lumen communicating with that opening. A dilute saline solution is pumped into the lumen and out through the side opening at a fixed rate, while the catheter is steadily withdrawn from the urethra at a substantially constant speed. A plot of the back pressure in the line between the pump and the side opening, against the physical distance of the opening along the urethra, yields the UPP. Typically, as the opening passes a location of constriction, whether normal or abnormal, the back pressure rises, and appears as a spike or hump in the graphical representation of pressure as a function of distance. A further parameter derived from UPP testing is what is called the maximum urethral closure pressure, which is the difference between the maximum pressure derived by the UPP test and the intravesical pressure of the bladder.

What are known in the art as membrane catheters are closed systems also used in obtaining UPPs. Here, the liquid that enters the catheter under pressure serves to expand a thin balloon or elastic element which is located adjacent the end of the catheter. The fluid is captive in the balloon and cannot flow out of the catheter. Single or double membrane catheters are frequently used for recording such urethral pressure profiles. As they are manually or mechanically withdrawn from the bladder cavity, the balloons will traverse the entire length of the urethra and serve to transmit pressure through the liquid with which they are inflated back to a chart recorder or other type of recording device.

A high pressure point in a UPP may be due to poor compliance or obstruction. As UPP procedures rely on very sensitive and indirect measurement, which is not always repeatable, perfusion profilometry is often replaced by the use of catheter micro-tip transducers that record pressure directly. Despite methodology, the diagnostic value of static UPP is limited because it is a study that is performed neither during filling and/or storage, nor during emptying. Static infusion profilometry does have value in evaluating artificial sphincter function, or a potential site of obstruction.

In the paper of Schafer et al. "Obstructed and Unobstructed Prostatic Obstruction: A Plea for Urodynamic Objectivation of Bladder Outflow Obstruction in Benign Prostatic Hyperplasia, Urology, [month] 1989, Vol. _, No. 6, pp. 198–203, the following assessment is noted in the summary: "The pathophysiological concept for transurethral resection of the prostate for the treatment of symptomatic benign prostatic hypertrophy centers around "prostatic obstruction." This blind study using advanced computer-assisted analysis of urodynamic pressure/flow studies confirms previous reports to the effect that a significant number (>25%) of patients undergoing prostatectomy objectively have no obstruction." Schaefer et. al conducted a trial on 39 patients who later went on to have a TURP. During the trial advanced level pressure flow studies were conducted on all the patients suspected to have prostatic obstructions. These patients were divided into three groups with all receiving a TURP. The urodynamic outcomes were then measured following recovery. The table below illustrates the urodynamic improvements according to the minimal urethral opening pressure (pmuo). These patients were arbitrarily referred to as "unobstructed," "obstructed," or "severely obstructed" according to the measured pmuo.

|  |  | Pre-op. | Post-op. |
| --- | --- | --- | --- |
| All patients | Residual Vol. | 129 ml | 64 ml |
| n = 39 | $Q_{max}$ | 7.5 ml/sec | 16.7 ml/sec |
| mean values | SD | −2.96 | −1.56 |
| Unobstructed | Residual Vol. | 156 ml. | 142 ml. |
| [UO] n = 10 | $Q_{max}$ | 10.7 ml/sec | 12.9 ml/sec |
| pmuo <25 cm $H_2O$ | SD | −2.47 | −2.14 |
| Obstructed | Residual Vol. | 50 ml | 53 ml |
| [O] n = 9 | $Q_{max}$ | 10.3 ml/sec | 12.5 ml/sec |
| pmuo 25–40 cm $H_2O$ | SD | −2.55 | −2.19 |
| Severely obstructed | Residual Vol. | 148 ml | 29 ml |
| [SO] n = 20 | $Q_{max}$ | 4.7 ml/sec | 20.8 ml/sec |
| pmuo >40 cm $H_2O$ | SD | −3.4 | −0.93 |

Urologists specializing in this field would recognize that only the severely obstructed patients had good urodynamic improvement and significant reduction in the PVR. The "obstructed" patients experienced slight improvement in urine flow rates, however, this improvement was arguably so minimal that the TURP procedure may not have been considered sufficiently beneficial to justify the discomfort and attendant risks of the procedure. The result of this study illustrate that in 20 of the 39 patients who received the TURP benefitted greatly. These patients were those with minimal urethral opening pressures of >40 cm $H_2O$.

Due to the fact that BOO patients are only a subgroup of patients with LUTS, proper treatment of the specific problem requires complete knowledge of the urodynamic status of the patient in order determine whether the patient's symptoms are caused by BOO, or from bladder deficiencies (e.g., bladder decompensation), or sphincter dysnergia. While comprehensive knowledge of the bladder-urethra interaction during urination may be obtained using complex urodynamic procedures, and UPP, most urologists are currently reluctant to perform such procedures prior to invasive, or minimally invasive, procedures directed to debulking the prostatic urethra. Furthermore, from the aforementioned discussion of cystometry, UPP, and pmuo, it may be appreciated that assessing the likelihood of improvement of the patients urine flow parameters following a dis-obstruction therapy such as TURP is possible, it is not however straight forward, without risk, and subject to a great deal of uncertainty.

It is the objective of the assembly and attendant methodology of the subject invention to provide the urologist additional clinical diagnostic information. The diagnostic assembly of the subject invention provides core information which are at least in part being sought by both the cystometry and UPP, however, unlike either of these procedures, the subject invention provides for dynamic fluid assessment, and further provides for the profiling of the urethra at a specific contact pressure, and simultaneously permits assessment of the effect of pressure on the entire prostatic urethra which may optionally include the external sphincter region.

SUMMARY OF INVENTION

The subject invention, whether it be the assembly, or the attendant methodology, provides for the easy acquisition of reliable diagnostic information by allowing the patient's true urination patterns to be observed and the physiological workings of the prostatic urethra ascertained in association therewith.

A diagnostic urethral assembly, preferably in the form of a kit, is generally provided. The assembly includes an elongate body having a fluid passageway and an elongate support member selectively positionable within the fluid passageway of the elongate body. The elongate body has a radially responsive wall segment, the elongate body being positionable within a lower urinary tract such that the radially responsive wall segment is adjacent a prostatic urethra. The elongate body is adapted to be in fluid communication with a bladder. The assembly has a first operably selective condition wherein the elongate support member is translatable relative to the elongate body so as to permit sequential and incremental radial compression of the radially responsive wall segment by the prostatic urethra in furtherance of defining architecture associated with the prostatic urethra. The assembly further has a second operably selective condition wherein fluid distally introduced into the elongate body radially expands the radially responsive wall segment into conforming engagement with the prostatic urethra in furtherance of obtaining a mold of same.

The subject invention seeks to provide the urologist with first, the ability to assess the flow of urine in an actual urination cycle to determine the contribution of flow rate/pressure irregularities on bladder outlet, prostatic urethra, and external sphincter. This is accomplished by the selective movement of an elongate support member within a body of the assembly which will receive the flowing urine at any point along these regions of the urethra while allowing the natural anatomic restrictions to effect the flow by providing a collapsible region in the catheter which is easily responsible to any restrictive regions.

The subject invention further seeks to provide for the assessment of the compressive regions of the urethra by forming a mold, casting or impression of the interior of the urethra at specific pressure conditions. Similar to a UPP, the measurement provides useful information about the compliance of the urethra along its length, however, in contradistinction to a UPP, it provides the ability to ascertain the opening pressure of the urethra while simultaneously identifying the exact location of the obstruction which is effecting the flow.

The foregoing and other objects, features, and advantages of the invention will be apparent with reference to the figures, the DETAILED DESCRIPTION OF THE INVENTION, and the claims hereinafter. The figures are not necessarily to dimensional or geometric scale, nor do they necessarily represent structures in accurate or representative relative scale. Emphasis rather is placed upon illustrating principals of the invention in a clear manner.

BRIEF DESCRIPTION OF THE DRAWINGS

FIG. 5 depicts the elongate support probe of the diagnostic urethral assembly of the subject invention;

FIG. 5A is an end view taken along the line A—A' of FIG. 5;

FIG. 8 depicts an impression or casting of a urethral segment with a low compliance prostatic urethra region; and, FIG. 9 depicts an impression or casting of a urethral segment with a high compliance prostatic urethra region.

DETAILED DESCRIPTION OF THE DRAWINGS

Figure 1:
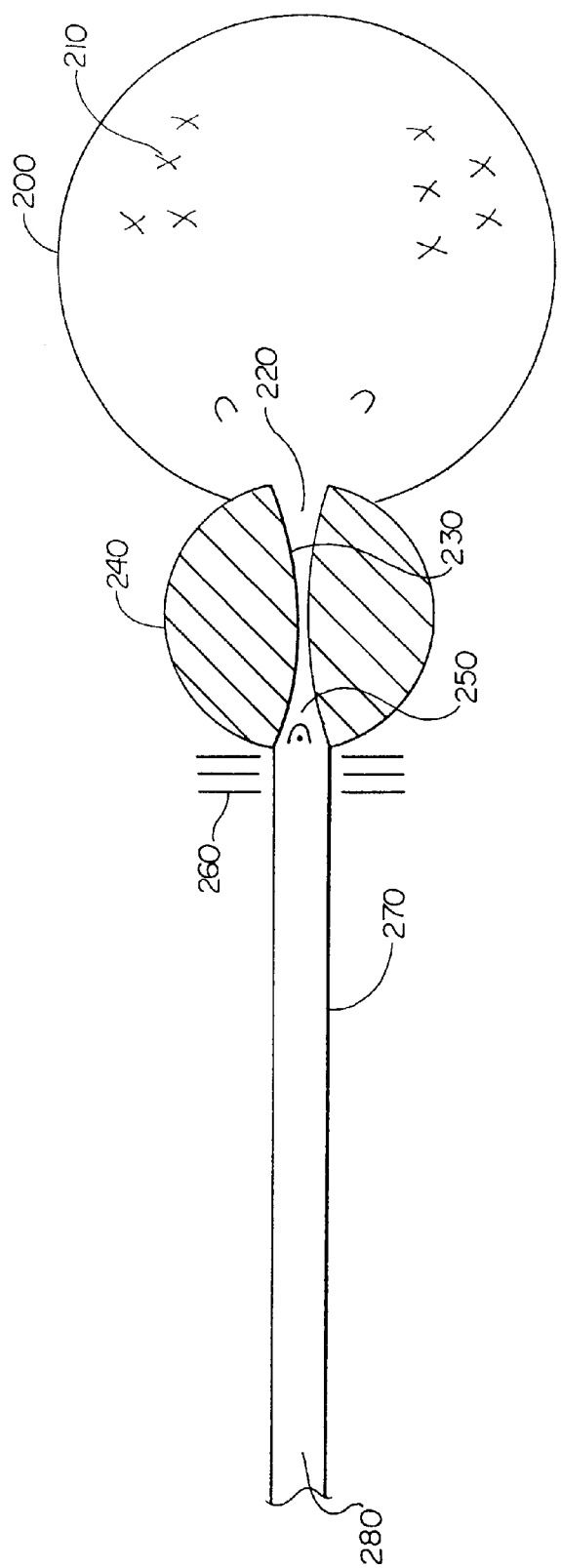
FIG. 1 depicts the human male urinary bladder and urinary passage.

The male urinary bladder, the urinary passage therefrom, and the structures associated therewith, hereinafter the lower urinary tract, are diagrammatically depicted in FIG. 1, with the cooperating indwelling structures of the diagnostic urethral assembly of the subject invention generally shown in FIG. 2, positioned with respect to the lower urinary tract. A critical feature of the assembly of the subject invention, in furtherance of differential LUTS diagnosis, is a radial responsive wall segment of an assembly body for engagement with a portion of the urethra, namely the prostatic urethra. Briefly, the radial responsive wall segment (i.e., diaphragm) possesses a dual functionality, namely inward and outward radial responsiveness, a selective functionality contingent upon the of the sought after diagnostic parameter (s). First, in furtherance of discharge flow analysis (e.g., UPP), the responsive body segment is progressively (i.e., sequentially and incrementally) "deactivated" (i.e., unsupported) so as to permit radially responsiveness in an inward direction due to the physiological action of the prostatic urethra thereupon, while qualitatively and/or quantitatively assessing fluid pressure and/or fluid flow for each step-wise or incremental deactivation. Second, in furtherance of ascertaining and memorializing the nature of the urethral structures, namely the architecture of the prostatic urethra and the relationships among the structures thereof, a molding or casting agent is introduced under pressure into the body of the assembly so as to permit radial responsiveness in an outward direction, the radially responsive wall segment being thereby substantially compliant with the prostatic urethra, and a casting being thusly obtainable.

Figure 2:
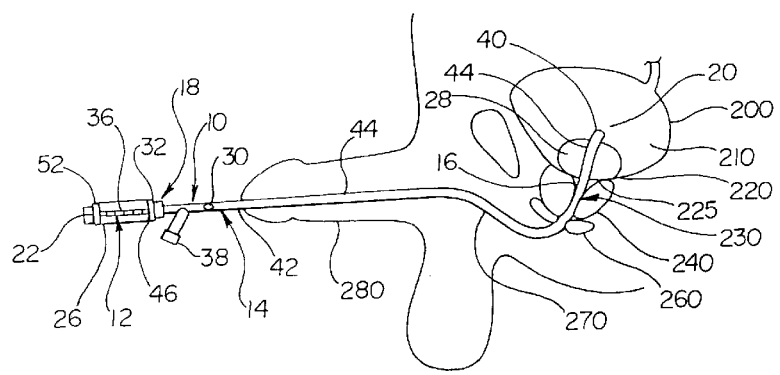
FIG. 2 depicts the cooperating indwelling structures of the diagnostic urethral assembly of the subject invention positioned with respect to the lower urinary tract.
Figure 3:
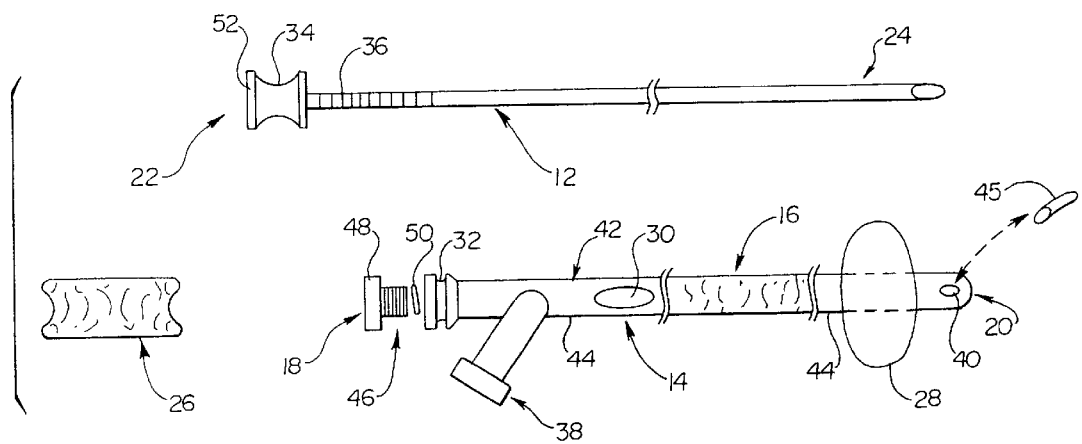
FIG. 3 illustrates the individual components or structures of the assembly of FIG. 2.

Referring again to the drawings, wherein like elements are assigned identical reference characters, and more particularly to FIGS. 2 and 3, the diagnostic urethral assembly 10 of the subject invention includes an elongate support member 12 receivable within an elongate body 14. The elongate body 14, positionable for fluid communication within the bladder 200, has a radial responsive (i.e., pliable) wall segment 16 for engagement with the prostatic urethra 230, and a distal end or extremity 18 opposite a free end 20 thereof. The elongate support member 12 (e.g., a probe) selectively supports or stents the pliable segment 16 of the assembly body 14, and portions of the prostatic urethra 230 thereby. The elongate support member 12 is adapted to be in fluid communication with the elongate body 14, and generally includes a distal end or extremity 22 opposite a free end 24 thereof. As will be later detailed, a resilient element 26 joins the distal end 22 of the support member 12 to the distal end 18 of the elongate body 14 so as to, among other things, facilitate co-action of said structures in furtherance of fluid flow examinations.

The assembly 10 generally has a first operably selective condition (e.g., FIGS. 2, 4, and 6–6C) wherein the elongate support member 12 is distally retractable (i.e., longitudinally translatable) relative to the elongate body 14 so as to permit the prostatic urethra 230 to sequentially and incrementally act upon the pliable wall segment 16 of the elongate body 14 in a physiological manner in furtherance of associating pressure and/or fluid flow deviations with urethral structures. A second operably selective condition for the assembly 10 of FIGS. 2 and 3 (e.g., FIG. 7) includes distal introduction of a mold forming agent under pressure into the elongate body 14 so as to expand the pliable wall segment 16 of the elongate body 14, thereby substantially conforming the pliable wall segment 16 to or with the prostatic urethra 230 in furtherance of obtaining a casting (i.e., a preserved impression) of the prostatic urethra architecture.

Referring now to FIG. 2, the diagnostic urethral assembly 10 has an outer catheter type body 14 which preferably includes an anchoring mechanism 28, supported at the free end or proximal extremity 20 thereof, which is positioned within the bladder 200, and an inner elongate support member 12 which is movable (i.e., translatable) within a passageway or lumen 30 of the elongate body 14. A sleeve 26, preferably a transparent (i.e., non-opaque) bellows, is reversibly secured, as by elastic retention or other known means, to a first grip recess 32 of the body 14 and a recess 34 of the elongate support member 12. The sleeve 26 provides for cooperative engagement between the elongate support member 12 and the elongate body 14, with its non-opaque character permitting visualization of gradient marks 36 which longitudinally extend throughout at least a portion of the length of the support member 12 (e.g., the distal portion thereof).

The resiliently linked elements of the diagnostic urethral assembly 10 permit fluid (e.g., urine, saline, etc.) to distally drain from the bladder 200 while simultaneously monitoring fluid flow rate and/or pressure. The reversibly retractable graduated support member 12 may be sequentially and incrementally shifted along the longitudinal axis of the assembly body 14 by grasping the distal extremity 22 of the graduated support member, and by further grasping the assembly body 14, while slowing separating the support member 12 from the body 14 (i.e., distally translating the elongate support member 12 relative to the assembly body 14). When this incremental shift occurs, the external pressure applied by the bladder outlet 225, prostate 240, or external sphincter 260 forces the pliable or placid segment (e.g., thin walled segment or diaphragm) 16 of the assembly body 14 radially inward, at least that portion of the radially responsive segment 16 adjacent (i.e., proximally adjacent) the proximal extremity 24 of the elongate support member 12. In a sense, a stenting function for the support member 12 is selectively "deactivated" to permit a step wise physiological response in the radially response segment 16 of the assembly body 14.

Any significant change in the rate of the fluid flow is readily and easily observed, either via the non-opaque sleeve 26 and/or via a fluid discharge port as will be later described. As the support member 12 is provided with incremental gradient markings 36, monitoring of the movement of the support member 12 with respect to the distal extremity 18 of the assembly body 14, simultaneously with the changes in the flow rates of discharged fluid, it may be easily differentiated whether an obstruction of fluid flow is being introduced by the bladder outlet 225, prostate 240, external sphincter 260, or a lesion elsewhere along the urethra 270.

Referring now to FIG. 3, the body 14 of the assembly 10 is shown having a distal extremity 18 opposite a free end 20 (i.e., proximal extremity). The anchoring mechanism 28, preferably but not necessarily in the form of a reversibly expandable element, such as a balloon or the like, secures the assembly body 14, in addition to aiding in the positioning thereof, in the lower urinary tract. The balloon 28, which is shown in an expanded state, is generally expandable about a proximal portion of the assembly body 14 for engagement with the bladder neck 220, as by the introduction of sterile or other physiologically compatible fluid into an inflation port 38 (e.g., a female luer fitting) using a syringe or other known fluid delivery methodology. Such anchoring arrangements are well known for urethral catheters, with a variety thereof equally suitable for the purpose of securably positioning the assembly body. The balloon 28, of known material, is preferably attached circumferentially about the proximal portion of the assembly body 14 by silicone adhesive from NuSil Technology (MED1-4213), with a primer coat (CF2-135) optionally applied to assist in bond adhesion.

Adjacent the proximal extremity 20 of the body 14, an orifice 40 provides a pathway for fluid communication (i.e., ingress) into the interior of the body 14 of the assembly 10. The assembly body 14 further has a passageway or lumen 30 which extends from the proximal 20 to distal 18 extremity thereof. The wall 42 traversing the proximal 20 and distal 18 extremities of the body 14 includes a radially responsive or pliable segment 16, and less pliable (i.e., more rigid) portions 44 adjacent thereto. The pliable segment 16 is characterized as being easily collapsed beneath any obstruction within the prostatic urethra 230. The fluid receiving orifice 40 of the body 14 is positioned near the proximal extremity 20 thereof, and is in communication with the fluid passageway 30.

Referring now to FIGS. 2 and 3, the assembly body 14 insertion sequence is as follows. The balloon 28 is initially in an unexpanded state. The support member 12 is completely inserted into the lumen 30 of the assembly body 14, with the proximal extremity 24 of the support member 12 positioned to be adjacent or near the proximal extremity 20 of the assembly body 14. This is accomplished by the introduction of the proximal extremity 24 of the support member 12 into the distal extremity 18 of the body 14, and fully advancing the support member 12 into and through the fluid passageway 30 of the body 14 until no further progress is achieved. A compression nut 48, receivable in the distal end 18 of the body 14, and part of a compression fitting assembly 46, is loosened slightly, as by rotating in a counter-clockwise direction from a closed or sealed condition. Rotation of the compression nut 48 will either compress or release a compression ring 50 of the compression fitting assembly 46. The support member 12 is then advanced into the lumen 30 of the body 14 until a grip 52 of the support member 12 is in contact with the fluid compression nut 48, at which point the compression nut 48 is then gently turned clockwise in order to secure the elongate support member 12 in position. The exterior of the assembly body 14 is then lubricated with KY or Lydicane jelly, or other urethral lubricants, followed by the entire assembly being inserted into the penial urethra. The assembly is then gently pushed towards the bladder 200 via the support member 12, and after sufficient length has been introduced to support the body 14 generally, the balloon 28 is expanded by the introduction of fluid into the luer fitting 38 using a 5 or 10 cc syringe. The balloon 28 is filled according to the physician's assessment of the requirements for the user's bladder, with an average of approximately 5 cc being typical.

Following the filling of the balloon 28, the assembly 10 is gently pulled distally by placing tension on the body 14. A slight tensile resistance experienced by the clinician acknowledges that the distal surface of the balloon 28 is gently pressing against the bladder neck 220, and that the body 14, and assembly thereby, is anchored in place. This is the intended location for the assembly 10, the radially responsive segment 16 of the body 14 substantially traversing the prostatic urethra 230.

Once the physician or clinician is satisfied that the diagnostic urethral assembly 10 is properly positioned, the support probe 12 may be selectively removed by simply sliding it out of the interior 30 of the body 14 via manipulation of the compression fitting assembly 46. Cooperative linkage of the support member 12 to the assembly body 14 is preferably, but not necessarily, completed at this point. The distal ends 22, 18 of the support member 12 and the body 14 are adapted to receive each of the opposing ends of the sleeve 26, more particularly, the receptive recess 32 of the body 14 and the receptive recess 34 of the support probe 12 receive the ends of the sleeve 26.

The sleeve 26, which is sufficiently dimensioned and resilient, respondingly elongates to accommodate the longitudinal movement of the support probe 12 relative to the body 14. Furthermore, the sleeve 26, in combination with the compression fitting assembly 46, form a distal most fluid boundary (i.e., delimit a variable fluid volume for the body of the assembly) for fluid sealing of the annular space existing between the support member and the body.

Figure 4:
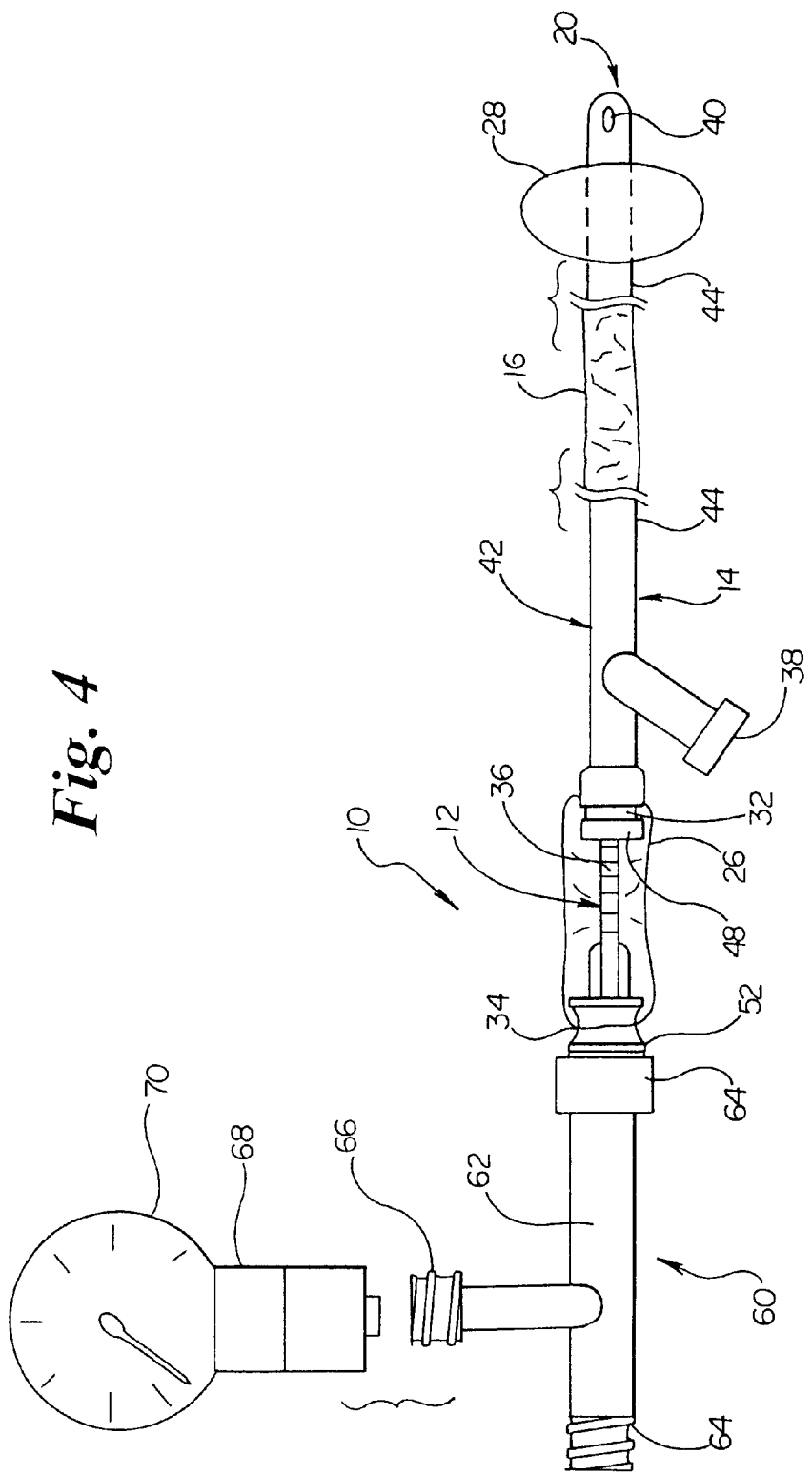
FIG. 4 illustrates structures of the diagnostic urethral assembly of the subject invention in cooperative engagement, more particularly, a pressure sensing apparatus is shown integral to the assembly structures of FIG. 3.

Referring now to FIG. 4, the graduated support member 12 is shown in cooperative engagement with the body 14 of the assembly 10. The assembly 10, as shown, further and preferably includes a pressure sensing apparatus 60. The pressure sensing apparatus 60 generally includes a manifold 62 which is preferably trifurcated, having fluid ingress and egress ports 64, and a port 66 available for pressure monitoring. An isolation coupling 68 and a pressure indicator (e.g., gauge) 70 are further illustrated, the particulars and equivalents of which are likewise well known to those of ordinary skill in the subject art. The pressure gauge 70 is preferably provided with a range of 0 to 200 cm $H_2O$ or equivalent units. Further explanation of the use of manifold 62, isolation coupling 68, and pressure gauge 70 will be given subsequently.

Referring now to FIGS. 5 and 5A, the graduated support member 12 is shown independent of the body 14 of the assembly 10. At least a single port 72 (i.e., orifice) is located near the proximal extremity 24 of the graduated support member 12, with a plurality of ports shown in the figure. The port or ports 24 provide fluid communication a passageway 74 interior to the graduated support member 12, and allow entry of urine 210 (FIG. 2) into the interior passageway 74 with a minimal restriction of flow. Passageway 74 communicates with port(s) 72 and the distal extremity 22 at an outlet 76.

Figure 6A:
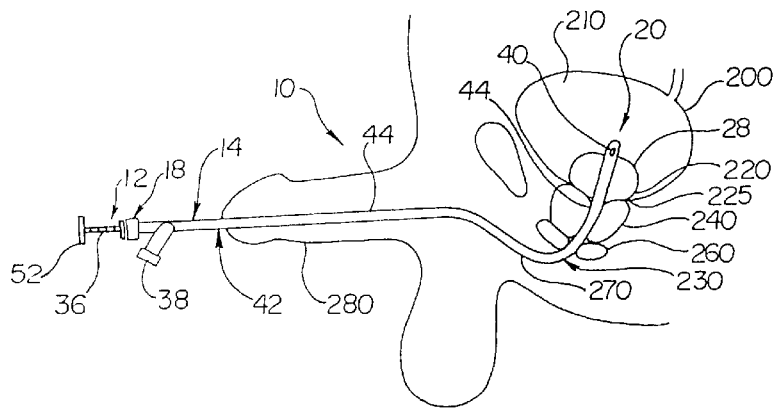
FIGS. 6–6C illustrate a progressive, sequential, incremental movement of the support probe relative to the assembly body during a diagnostic episode.
Figure 6B:
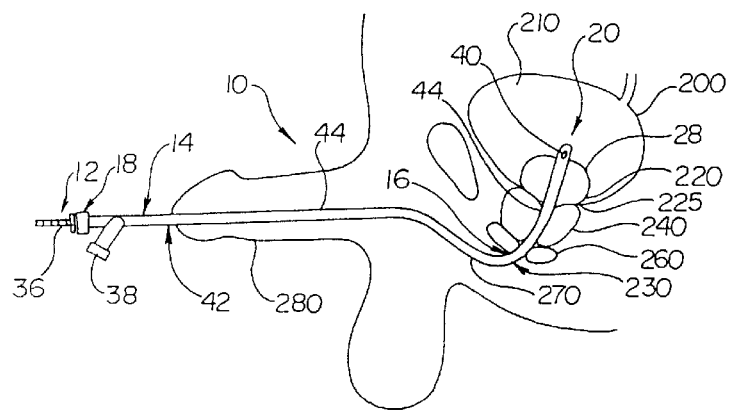
Figure 6C:
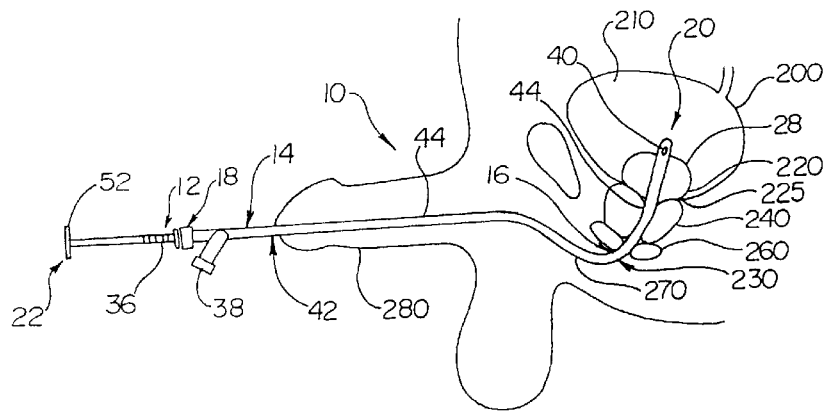

Referring now to FIGS. 6–6C, the critical functions of the assembly essential to a UPP differential diagnosis are illustrated. These figures illustrate a selective progressive movement of the graduated support member 12 within the interior 30 of the body 14. These in-situ illustrations are shown without the sleeve 26 or the pressure feedback apparatus 60, each of which is shown and previously discussed in relation to FIG. 4, for ease of illustration.

To perform a first differential diagnostic procedure, the bladder 200 needs to contain either urine or be filled with fluid. A minimum bladder volume to initiate a micturition cycle is about 200 cc, and in some patients with decompensated bladders, as much as 400 or even 600 cc may be required. The volume of fluid required in the filling of the bladder is significant and essential information in any bladder diagnostic procedure. Once bladder 200 is filled, the patient is asked to stand or sit up and urinate. The urination is either performed into a portable urinal, or a uroflowmetry machine which will record the rate of flow and volume collected. As the patient voids the body 14 of the assembly 10 is held stationary while the graduated support member 12 is gradually retracted. By observing the appearance of the fluid flow as the graduated support member 12 is moved longitudinally, any obstruction within the urethra 270, more particularly, in that region (i.e., length) proximally adjacent the free end 24 of the support member 12, will compress the radially responsive segment 16 the body 14. As may be appreciated, the relatively radially rigid surface of the graduated support member serves a function of selectively supporting (i.e., stenting) at least the radially responsive segment 16 of the body 14 of the assembly 10.

An understanding of the differential diagnosis is best explained by examination of FIGS. 6–6C which illustrate a progressive, sequential, incremental movement of the support probe 12 relative to the assembly body 14 during a diagnostic episode. During the release of fluid by the support member 12 relative to the body 14, and while observing the position of the graduations 36 of the calibrated support member 12 in relation to the distal extremity 18 of the body 14, the effects of obstructive contribution of bladder outlet 225, prostatic urethra 230, and the external sphincter 260 may be observed, and thereby ascertained as the fluid flow would normally continue uninterrupted by this region of the urethra.

For instance, if the fluid flow discharge rate is 14 cubic centimeters per second (cc/s), in the location shown in FIG. 6, and it drops substantially, perhaps more than 2 cc/s as it moves to location 6A, it will become evident to the urologist, or other trained observer, that the bladder outlet 225 or bladder neck 220, is causing some restriction. If the change in fluid flow discharge rate were 5 cc/sec, therefore reducing the discharge rate to 7 cc/sec, the drop would be very excessive. As urine 210 is being discharged through the support member 12, if an obstruction is present within bladder outlet 225, the fluid flow rate or pressure will drop. When the calibrated support member 12 is moved outwardly within the interior 30 of the body 14 (i.e., distally with respect to the body), and an obstruction exists in the prostatic urethra 230, and not in the internal sphincter, as is illustrated in FIG. 6B, the fluid flow rate and pressure will drop. FIG. 6C illustrates an example of no obstruction being present within either the bladder outlet 225 or the prostatic urethra 230, a restriction however being present in the external sphincter 260. In this situation the discharge rate and pressure would be maintained until the calibrated support member 12 reached a position within the body 14 which did not provide any internal support (i.e., radially outward) of the pliable segment 16 of the body 14. The distance traveled from the initiation of flow will allow the user to determine reasonably accurately whether any drop in discharge rate is caused by either the bladder outlet 225 or the prostatic urethra 230. Confirming that any drop in discharge rate is from the external sphincter 260 is more difficult due to the greatly varying lengths of the prostatic portion 230 of the urethra 270. These lengths may be as little as 1.5 centimeters (cm) to as long as about 7 cm.

Prostatic obstructions are frequently within the proximal most portion of the prostatic urethra, very near the bladder outlet. It may be appreciated that through the procedures outlined, and by the assembly components so far detailed, one may clinically determine the level of discharge flow reduction relative to the anatomical location. Pressure and flow reductions during longitudinal movements of the support member may be a step function if there are abrupt resistance due to the any of the three primary structures.

It is appreciated by urologists who diagnose bladder outlet difficulties that often inability to satisfactorily empty the bladder is often the result from multiple problems. It is possible for a weak bladder to be the cause of low flow rate, alternately, a ledge at the bladder outlet is known to interfere with discharge flow. Since the bladder outlet twists and collapses simultaneously as it closes, the urethra in this part of the anatomy is often referred to as an internal sphincter. This language is common, though use of this term is usually qualified with the clarification that it is really the bladder outlet and that technically it is not a sphincter.

By observing the flow patterns throughout the complete available movement of the calibrated support member within the body, the urologist is able to get a reasonably good assessment of the anatomical origins of the detected discharge flow problem. The driving pressure range during the micturition cycle of the bladder for a competent bladder should range from 8 to 20 cm $H_2O$. In the event that the bladder is producing pressures substantially below this, the flow rate of urine will be quite low. These patients would be candidates for further evaluation to determine if their difficulties in urination may be attributed to decompensated bladders. Patients with static pressures far in excess of this may have non-compliant bladders. For non-compliant bladders, the flow rates may be substantially large when the prostate is stented. In this circumstance, the volume of urine that the bladder can store is very small. For this reason, when the bladder is being filled, observing the volume and the pressure may be very useful in assessing the urodynamic status of the patient.

Patients undergoing these pressure profile assessments such as those introduced in the previous discussions are being considered primarily for dis-obstruction intervention for what is suspected of BPH. This emphasizes the importance of understanding the actual effect on discharge flow rate that the urethra has throughout and along its length. When the procedures of complex urodynamic assessments are not performed, the level of uncertainty in the diagnosis may be as great as 50% depending on the factors considered and screening procedures used in arriving at the diagnosis. The current American Urological Association (AUA) guidelines do not recommend use the complex urodynamic assessments in diagnosing BPH prior to performing TURP. As may be appreciated from the background discussion, this level of understanding leaves a substantial percentage of patients without urodynamic improvements following surgery, while still participating in the co-morbidities of that procedure which include impotence, retrograde ejaculation (i.e., semen goes to the bladder), infection, hematuria, incontinence and others.

The use of these differential diagnosis steps to evaluate the urine flow study is very useful and desirable. This information provides an increased confidence level in identifying the source of the flow resistance. It should be apparent that it is very important to understand exactly where the calibrated support member is within the interior of the body, as this provides an understanding of the pressure-flow characteristics at a given location. Since prostate length varies substantially, it is difficult to know when the support member is satisfactorily positioned in the prostate or urethra. The length of the prostatic urethra is normally assessed using either cystoscopy which involves inserting a large fiberoptic into the interior the urethra for measurement, or using trans-rectal ultrasound (TRUS) which involves placing a large ultrasound probe into the rectum and measuring the prostate from a posterior projection. Measurement of lengths with TRUS is of relatively low accuracy and repeatability, thus, for this reason it will be clear why the further features of this invention are important.

In order to gain a more comprehensive understanding of the lengths of the prostatic urethra and the level of obstruction which may be effecting the urine flow, another feature of this differential diagnosis procedure involves the use of a quick setting rubber-like compound to make a flexible three dimensional cast of the select segments of the urethra. As will be discussed shortly, the analysis of the casting provides the necessary understanding of the lengths and mechanical nature of the prostatic urethra, an understanding which diminishes the uncertainty of the underlaying source of the symptom(s).

Figure 7:
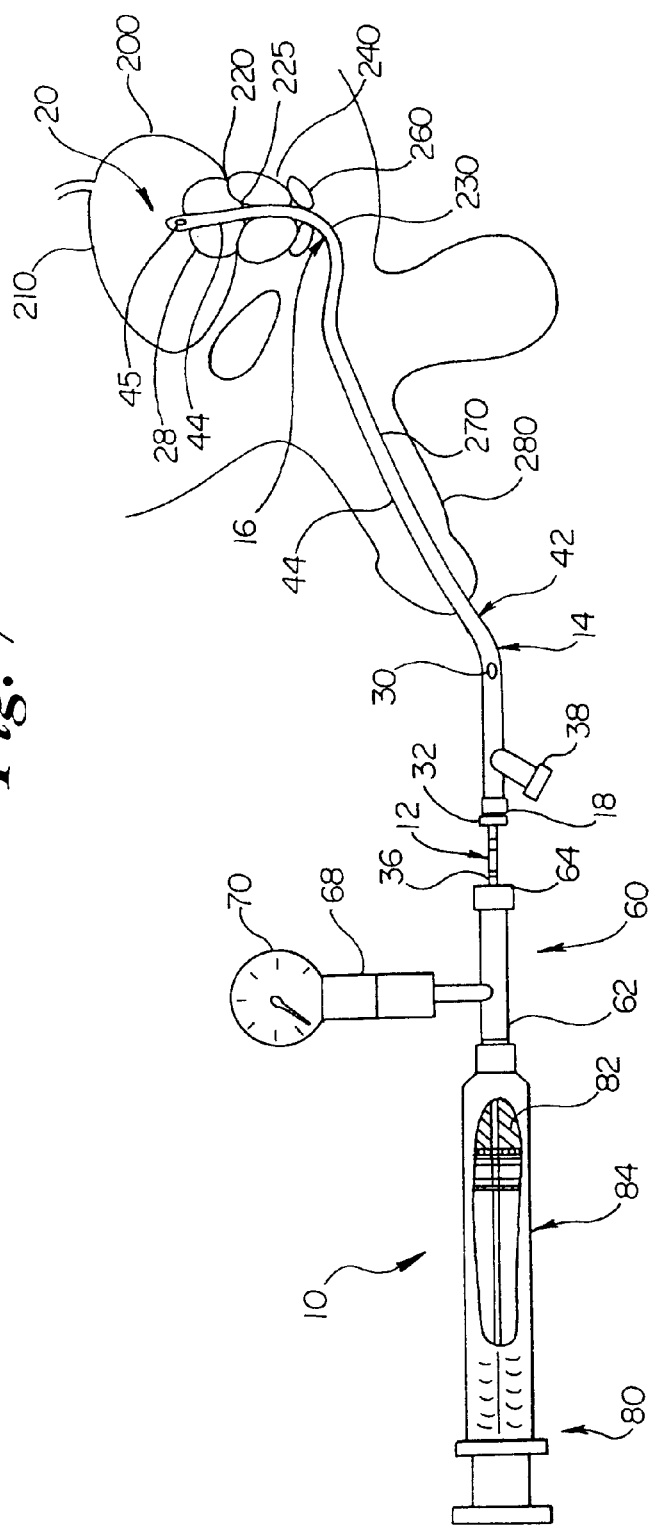
FIG. 7 depicts the diagnostic urethral assembly structures of FIG. 4 supplemented with the impression apparatus for introducing an impression agent for forming a casting of the prostatic urethra.

Referring now to FIG. 7, the diagnostic urethral assembly structures of FIG. 4 are shown supplemented with an impression apparatus 80 for introducing an impression or casting agent 82 for forming a casting 800, 900 as shown in FIGS. 8 and 9 respectively, of the prostatic urethra. Prior to the initiation of the impression procedure, the calibrated support member or probe 12 is removed from the interior 30 of the body 14 and flushed with saline or the like. A plug 45 (FIG. 3), preferably of silicone is then inserted into the proximal extremity 20 of the body 14 of the assembly 10, as by introducing it through the interior of the compression nut 48. The calibrated probe 12 is than re-introduced into the body 14 until it is fully advanced, as previously outlined with respect to the flow study methodology. The sleeve 26 may be omitted from the assembly 10 during this diagnostic technique, as there is no fluid flowing from the bladder through the assembly body (i.e., fluid, namely a casting agent, radiates outwardly from the elongate support member in this methodology as opposed to a fluid, namely urine, saline, etc., radiating inwardly toward the elongate support member as in the fluid flow diagnostic).

Following re-insertion, the calibrated support probe 12 may be gradually shifted along the longitudinal axis of the body 14 by holding the body 14 in one hand and a syringe 84 in the other. The syringe 84 is filled with a low viscosity impression material 82 and is conducted to the proximal extremity 20 of the body 14 by the support probe 12. As the impression material 82 fills the interior 30 of the body 14 in the placid segment 16, the support probe 12 is slowly withdrawn therefrom. This results in the filling of the body 14, namely the fluid passageway 30, with impression material 82. At this point of "deactivation", the external pressure applied by the bladder outlet 225, the prostate 240, and the external sphincter 260 may force the radially responsive segment 16 of the body 14 radially inward. The saline within the pressure isolation coupling 68 prevents the impression material 82 from entering pressure indicator 70. During filling of the interior of the placid segment 16 of the body 14, the compression nut 48 is left slightly loose to allow for the air, saline, or urine with which the interior was flushed with or had present therein, to exit the interior 30 of the body 14 as it is displaced by the introduced casting agent 82. When filling is completed, the compression nut 48 is tightened. Pressure is sustained with the syringe 84, or other suitable pressure apparatus such as a compression bulb or the like.

The impression material 82, vis-a-vis the "closed" assembly 10, is sustained at a specific pressure which is intended to place an outward pressure on the body 14 for a preselected time, consistent with curing requirements of the impression material 82, so as to conform the placid segment 16 of the body 14 to the urethral segment 230 adjacent thereto. A sustained pressure of approximately 40 cm H$_2$O during curing will give a good indicator of the opening pressure of the urethra to indicate severity of obstruction. The impression material will then cure at that pressure, with the shape of the cured impression material (i.e., the casting resulting therefrom) providing the urologist with critical information about the characteristics of the urethra in the vital regions. The observance of the incremental gradient marks 36 of the support member 12 assist in uniform filling of the assembly body 12. An intact competent external sphincter will sustain bladder pressures of approximately 80 cm H$_2$O or more. Due to the strength of the external sphincter and the broad flaring out within the urethra distal of that landmark, the external sphincter should normally be very visible on the casting. Furthermore, with the balloon 28 positioned at the outlet of the bladder 220 so as to properly position and anchor the diagnostic assembly 10, the casting accurately reflects and memorializes the length of the prostatic urethra and the positions of both the bladder outlet and the external sphincter. The casting further provides a three dimensional model of the area available for urine flow along the impression length.

The casting is obtained by extraction or withdrawal of the diagnostic assembly 10, namely the integrated support member 12 and body 14, while in an assembled or disassembled condition (i.e., together or individually), with the pressure sensing apparatus 60 and impression apparatus 80 having been previously removed from the assembly 10. Fluid from the balloon 28 is released by withdrawal via syringe (not show) at the balloon filling port 38 positioned at the distal extremity 18 of the body 14, with the body 14 removed as easily as known urinary catheters. As the impression material is sufficiently compliant to allow easy flexure within the urethra during removal, no trauma is thereby caused. The preferred impression material is a two part vinyl polysiloxane having a set-up time of approximately 4 minutes at body temperature and a set durometer of only 30 Shore A. Curing is not inhibited by the presence of water based fluids such as urine or saline. The firmness of the cured material or casting is roughly equivalent to standard urinary catheters made of latex rubber or silicone. The casting is finally retrieved from the body of the assembly, as by cutting it therefrom or generally withdrawing it, inspected, measured and retained as part of the patient's medical record.

The body of the assembly may be sized from 8 to 24 French, however, the preferable size is 14 or 18 French, with the pliable segment or diaphragm easily expandable to up to 24 French. For most patients this is adequate expansion to determine prospective urodynamic influences. The relatively large expansion size in the radially responsive segment is selected to reflect the nature of the prostatic urethra. The purpose of this diagnostic procedure is to provide information specifically about the effects of bladder outlet obstructions which occupy the length extending from the bladder outlet to the bulbous urethra. It may be appreciated that the pliable segment may be lengthened in order to assess the presence of lesions within the urethra distal of the bulbous urethra, or otherwise modified to ascertain the nature and relationships among other lower urinary tract structures. The preferred length for the radially responsive segment is 15 cm or less, this length being generally sufficient to span from the bladder outlet to the bulbous urethra in most, if not all, males.

Referring now to FIG. 8, an impression 800 of a urethra with a low compliance prostatic urethra region, made at specific pressure conditions, is shown having been removed from the body of the diagnostic assembly. As previously noted, the casting is preferably, but not necessarily removed for more compact handling and storage. The impression 800 has a proximal extremity 802 and a distal extremity 804. Location or feature 806 shows the effect (i.e., nature) of the bladder outlet during the impression procedure. Location or feature 808 shows the effect of the prostatic urethra for a low compliance patient. Finally, location or feature 810 shows the effect of the external sphincter.

Referring now to FIG. 9, an impression 900 of a urethra with a high compliance prostatic urethra region, made at specific pressure conditions, is shown having been removed from the body of the diagnostic assembly. The impression 900 has a proximal extremity 902 and a distal extremity 904. Location or feature 906 shows the effect (i.e., nature) of the bladder outlet during the impression procedure. Location or feature 908 shows the effect of the prostatic urethra for a high compliance patient. Finally, location or feature 910 shows the effect of the external sphincter.

It is intuitive that when the three dimensional urethral impression proves that a minimal obstruction is present, such as is the circumstance with the casting of FIG. 9, a prostatic obstruction is not likely to be the source of the difficulty in urination. FIG. 8 illustrates a contrary diagnostic outcome. In this impression, it may be seen that the prostate is compressing the prostatic location, substantially leaving little area for fluid flow. In this situation, it would appear likely that the prostate was at least in part a contributory factor of LUTS. In this scenario, a disobstructive therapy diagnosis is likely to be reinforced.

The impression system of the diagnostic urethral assembly of the subject invention provides for a new approach to determining if the sphincters, or prostate, or lower urethral strictures are the underlying cause of the flow restrictions that some patients suffer from. The assembly, and attendant methodologies outlined herein, provide a more straight forward and accurate alternative to diagnostic and procedural options heretofore known, namely complex urodynamic assessments such as the use of video fluoroscopy simultaneously with the holding and release of urine, cystometry, urethral pressure profiling, ultrasonic volume assessments (PVR), and uroflowmetry, some of which the urological community are currently hesitant to perform on a broad spectrum basis. Due to the fact that the diagnostic assembly and attendant methodology of the subject invention are specifically for differentiation of sources of obstructions, it is beneficial and highly desirable for the urologist to use a body which is sized to the patients anatomy to insure that data obtained reflects true urethral dynamics, whether in flow/pressure outcomes, or cast geometry.

The objective of the invention is to provide the urologist with simple and gentle diagnostic urethral assembly and methodology for gaining a higher confidence in the diagnosis of BPH prior to or in lieu of aggressive clinical correction. The assembly of this invention allows for relatively simple flow examinations which aid obstruction detection, and location. Using the actual flow motivation of the bladder, the competency of the bladder is examined. The assembly, namely the combination of the body and the calibrated support probe, allows for data acquisition regarding the functionality of the entire proximal urinary tract. It should be further appreciated that, although there is an inherent value to the acquired flow information, like all urology flow information, some inconclusiveness about the cause of the insufficiencies or anomalies remains. The electrical activity relating the micturition cycle often varies widely between cycles, and the strength of the detrusor function of the bladder and relaxation of the sphincters also vary. For this reason, the second function that is enabled by the assembly of the subject invention, namely that of producing an impression of the urethra at specific conditions, is very important. The impressions are formed without the necessity of a full bladder, or active micturition. The impressions allow a valuable feature as either an adjunct to the flow differential diagnosis procedure, or independently, as does the flow differential diagnosis procedure.

What is claimed is:

1. A diagnostic urethral assembly comprising:
   a. an elongate support member having opposing first and second ends, said elongate support member being adapted to pass fluid therethrough; and,
   b. a urethral catheter positionable for communication with a bladder, said urethral catheter adapted to receive, and be in fluid communication with said support member, said urethral catheter having a placid segment positionable so as to traverse a prostatic urethra and be physiologically responsive to structures of a lower urinary tract, said elongate support member selectively supporting said placid segment, progressive retraction of said elongate support member permitting the structures of the lower urinary tract to physiologically act in a sequential and incremental manner upon portions of said placid segment, the action upon said placid segment resulting in an observable change in fluid dynamics in furtherance of lower urinary tract symptoms diagnosis.

2. The assembly of claim 1 wherein said elongate support member includes longitudinally extending graduations.

3. The assembly of claim 2 wherein said first end of said elongate support member is a distal end, said second end being a proximal end.

4. The assembly of claim 3 wherein said urethral catheter includes proximal and distal portions, said proximal portion of said urethral catheter being a free end thereof.

5. The assembly of claim 3 wherein said distal end of said elongate support member is adapted to receive a pressure sensing apparatus.

6. The assembly of claim 5 further comprising a pressure sensing apparatus.

7. The assembly of claim 6 wherein said pressure sensing apparatus includes proximal and distal ends, and a pressure indicator disposed therebetween.

8. A diagnostic urethral assembly comprising:
   a. an elongate support member having opposing first and second ends and longitudinally extending graduations upon a surface thereof, said elongate support member being adapted to pass fluid therethrough, said first end of said elongate support member is a distal end, said second end being a proximal end;
   b. a urethral catheter positionable for communication with a bladder, said urethral catheter adapted to receive, and be in fluid communication with said support member, said urethral catheter having proximal and distal portions, said proximal portion of said urethral catheter being a free end thereof, and a placid segment positionable so as to traverse a prostatic urethra and be physiologically responsive to structures of a lower urinary tract, said elongate support member selectively supporting said placid segment; and,
   c. a resilient linkage, said resilient linkage securing said distal end of said elongate support member to said distal portion of said urethral catheter, progressive retraction of said elongate support member permitting the structures of the lower urinary tract to physiologically act in a sequential and incremental manner upon portions of said placid segment, the action upon said placid segment resulting in an observable change in fluid dynamics in furtherance of lower urinary tract symptoms diagnosis.

9. The assembly of claim 8 wherein said resilient linkage is elongatingly responsive to retraction of said elongate support member relative to said urethral catheter.

10. The assembly of claim 8 wherein said resilient said resilient linkage is transparent.

11. The assembly of claim 8 wherein said longitudinally extending graduations of said elongate support member are visible through said resilient linkage.

12. The assembly of claim 11 wherein said resilient linkage comprises a sleeve.

13. The assembly of claim 11 wherein said resilient linkage comprises a bellows.

14. The assembly of claim 11 wherein said proximal portion of said urethral catheter includes an anchoring element for securing said urethral catheter within the lower urinary tract, and said assembly thereby.

15. The assembly of claim 14 wherein said anchoring element comprises a reversibly expandable member.

16. The assembly of claim 15 wherein said reversibly expandable member circumferentially extends about said proximal portion of said urethral catheter.

17. The assembly of claim 11 wherein said distal end of said elongate support member is adapted to receive a pressure sensing apparatus.

18. The assembly of claim 17 further comprising a pressure sensing apparatus.

19. The assembly of claim 18 wherein said pressure sensing apparatus includes proximal and distal ends, and a pressure indicator disposed therebetween.

20. The assembly of claim 19 wherein said pressure sensing apparatus includes a pressure recorder.

21. A diagnostic urethral assembly comprising:
   a. an elongate support member having opposing first and second ends and longitudinally extending graduations upon a surface thereof, said elongate support member being adapted to pass fluid therethrough, said first end of said elongate support member is a distal end, said second end being a proximal end;
   b. a urethral catheter positionable for communication with a bladder, said urethral catheter adapted to receive, and be in fluid communication with said support member, said urethral catheter having a placid segment positionable so as to traverse a prostatic urethra and be physiologically responsive to structures of a lower urinary tract, said elongate support member selectively supporting said placid segment, progressive retraction of said elongate support member permitting the structures of the lower urinary tract to physiologically act in a sequential and incremental manner upon portions of said placid segment, the action upon said placid segment resulting in an observable change in fluid dynamics in furtherance of lower urinary tract symptoms diagnosis;

c. a pressure sensing apparatus receivable upon said distal end of said elongate support member, said pressure sensing apparatus includes proximal and distal ends, and a pressure indicator disposed therebetween; and, d. means for introducing a mold forming substance into said urethral catheter so as to obtain a mold of the prostatic urethra, said means being joinable with said distal end of said pressure sensing apparatus.

22. The assembly of claim 21 wherein said mold forming substance fills a fluid passageway of said urethral catheter.

23. The assembly of claim 22 wherein said mold forming substance conforms said placid segment of said urethral catheter to architecture of the prostatic urethra so as to thereby form a casting reflecting the architecture.

24. The assembly of claim 22 wherein said mold forming substance radially expands said placid segment of said urethral catheter outwardly.

25. The assembly of claim 22 wherein said mold forming substance is conveyed to said fluid passageway of said urethral catheter under pressure.

26. A diagnostic urethral assembly comprising an elongate body having a fluid passageway and an elongate support member selectively positionable within said fluid passageway of said elongate body, said elongate body having a radially responsive wall segment and being positionable within a lower urinary tract such that said radially responsive wall segment is adjacent a prostatic urethra, said elongate body adapted to be in fluid communication with a bladder, said assembly having a first operably selective condition wherein said elongate support member is translatable relative to said elongate body so as to permit sequential and incremental radial compression of said radially responsive wall segment by the prostatic urethra in furtherance of defining architecture associated with the prostatic urethra, and a second operably selective condition wherein fluid distally introduced into said elongate body radially expands said radially responsive wall segment into conforming engagement with the prostatic urethra in furtherance of obtaining a mold of same.

27. A diagnostic urethral kit comprising:

a. a catheter securably positionable so as to be in fluid communication with a bladder and adapted to receive and pass urine therefrom, said catheter having a radially responsive wall segment for engaging a prostatic urethra, said radially responsive wall segment being physiologically responsive to structures of a lower urinary tract; and, b. an elongate tubular member receivable within said catheter, said elongate tubular member having a wall, opposing first and second ends, and a lumen, said wall extending between said opposing first and second ends and having longitudinally extending graduations, said elongate tubular member providing support for said radially responsive wall segment of said catheter, said elongate tubular member being selectively retractable from said catheter such that the structures of the lower urinary tract are permitted to physiologically act upon a portion of said segment adjacent said first end of said elongate tubular member.

28. A diagnostic urethral assembly comprising;

a. an elongate body, positionable for fluid communication with a bladder, said elongate body having a pliable wall segment for engagement with a prostatic urethra, and a distal end opposite a free end thereof;

b. an elongate support member receivable within said elongate body to selectively support said pliable wall segment and the prostatic urethra thereby, said elongate support member adapted to be in fluid communication with said elongate body, said elongate support member having a distal end opposite a free end thereof, said assembly having a first operably selective condition wherein said elongate support member is distally retractable relative to said elongate body to permit the prostatic urethra to sequentially and incrementally physiologically act upon said pliable segment in furtherance of defining architecture associated with the prostatic urethra, and a second operably selective condition wherein fluid distally introduced into said elongate body is acted upon such that said pliable segment substantially conforms to the prostatic urethra.

29. In a urethral diagnostic assembly including a urethral catheter having a radially responsive wall segment positionable to substantially traverse a prostatic urethra, means for regulated introduction of a casting agent at least indirectly into the urethral catheter such that the radially responsive wall section expands to engage the prostatic urethra, a dynamic casting being thereby formable to ascertain prostatic urethral architecture.

30. A diagnostic urethral assembly comprising:

a. an elongate support structure adapted to receive and pass fluid therethrough;

b. a urethral catheter having a radially responsive prostatic segment for traversing a prostatic urethra, said elongate support structure receivable within said urethral catheter for selective support of said radially responsive prostatic segment; and, c. a resilient sleeve for linking a distal end of said elongate support structure to a distal portion of said urethral catheter, progressive retraction of said elongate support structure relative to said urethral catheter permitting a prostate to physiologically act in a sequential and incremental manner upon portions of said radial responsive prostatic segment in furtherance of bladder outlet obstruction diagnosis.

31. A diagnostic urethral device comprising a tubular body having proximal and distal end portions, and a physiologically responsive flexible wall segment therebetween, said proximal end portion of said tubular body adapted to be anchored at a bladder neck of a lower urinary tract for urine ingress, said physiologically responsive flexible wall segment of said tubular body being adapted to transverse a prostatic urethra in furtherance of assessing prostate contribution to bladder outlet obstruction.

* * * * *